United States Patent [19]
Rodgers et al.

[11] Patent Number: 5,834,432
[45] Date of Patent: Nov. 10, 1998

[54] USE OF ANGIOTENSIN II TYPE 2 RECEPTOR AGONISTS IN TISSUE REPAIR

[75] Inventors: Kathleen Elizabeth Rodgers, Long Beach; Gere Stodder Dizerega, Pasadena, both of Calif.

[73] Assignee: The University of Southern California, Los Angeles, Calif.

[21] Appl. No.: 465,774

[22] Filed: Jun. 6, 1995

[51] Int. Cl.$^6$ ................................ A61K 38/00
[52] U.S. Cl. ................ 514/16; 514/15; 530/316; 530/327; 530/328
[58] Field of Search ............ 514/15, 16; 530/316, 530/327, 328

[56] References Cited

U.S. PATENT DOCUMENTS 5,015,629  5/1991  di Zerega .............................. 514/16

OTHER PUBLICATIONS

Hunt et al., *Coagulation and macrophage stimulation of angiogenesis and wound healing*, in *The surgical wound*, pp. 1–18, ed. F. Dineen & G. Hildrick–Smith (Lea & Febiger, Philadelphia: 1981).

Grotendorst, GR et al. (1985) Stimulation of granulation tissue formation by platelet–derived growth factor in normal and diabetic rats. J Clin Invest 76:2323–9.

Mustoe, TA et al. (1987) Accelerated healing of incisional wounds in rats induced by transforming growth factor–β. Science 237:1333–5.

Pierce, GF et al. (1988) In vivo incisional wound healing agumented by platelet–derived growth factor and recombinant c–sis gene homodimeric proteins. J Exp Med 167:974–87.

Lynch, SE et al. (1989) Growth factors in wound healing. J Clin Invest 84:640–6.

Greenhalgh, DG et al. (1990) PDGF and FGF stimulate wound healing in the genetically diabetic mouse. Am J Pathol 136:1235–46.

Kimura et al. Changes in skin angiotensin II receptors in rats during wound healing. Biochem Biophys Res Commun 187:1083–90, 1992.

Speth, RC ad KH Kim. 1990. Discrimination of two angiotensin II receptor subtypes with a selective agonist analogue of angiotensin II, p–amnophenylalanine6 angiotensin II. Biochem Biophys Res Commun 169:997–1006.

Catalioto et al. 1994. Angiotensins induce the release of prostacyclin from rabbit vas deferens: evidence for receptor heterogeneity. Eur J Pharmacol 256:93–97.

Bryson, SE et al. 1992. Induction of the angiotensin At2 receptor subtype expression by differentiation of the neuroblastoma x glioma hybrid, NG–108–15. Eur J Pharmacol 225:119–127.

Dzau V.E. et al. (1989) Molecular mechanism of angiotensin in the regulation of vascular and cardiac growth. J Mol Cell Cardiol 21 (Supple III):S7.

Berk, BC et al. (1989) Angiotenin II stimulated protein synthesis in cultured vascular smooth muscle cells. Hypertension 13:305–14.

Kawahara, Y, et al. (1988) Angiotensin II induces expression of the c–fos gene through protein kinase C activation and calcium ion mobilization in cultured vascular smooth muscle cells. BBRC 150:52–9.

(List continued on next page.)

*Primary Examiner*—Cecilia J. Tsang
*Assistant Examiner*—C. Delacroix-Muirheid
*Attorney, Agent, or Firm*—Knobbe Martens Olson & Bear LLP

[57] ABSTRACT

Angiotensin II Type 2 receptor agonists (AT2 receptor subtype agonists) are useful in accelerating wound healing. These compounds form the basis of compositions useful for accelerating wound healing, in which the active agent is present in an amount effective to accelerate wound healing. Preferably, the compositions are in the form of matrical or micellar solutions.

6 Claims, 2 Drawing Sheets

OTHER PUBLICATIONS

Naftilan, AJ et al. (1989) Induction of platelet–derived growth factor A–chain and c–myc gene expressions by angiotensin II in cultured rat vascular smooth muscle cells. J Clin Invest 83:1419–24.
Taubman, MB et al. (1989) Angiotensin II induces c–fos mRNA in aortic smooth muscle. Role of $Ca^{2+}$ mobilization and protein kinase C activation. J Biol Chem 264:526–530.
Nakahara, K et al. (1992) Identification of three types of PDGF–A chain gene transcripts in rabbit vascular smooth muscle and their regulated expression during development and by angiotensin II. BBRC 184:811–8.
Stouffer GA and GK Owens. (1992) Angiotensin II induced mitogenesis of spontaneously hypertensive rat derived cultured smooth muslce cells is dependent on autocrine production of transforming growth factor–$\beta$. Circ Res 70:820–828.
Wolf, G et al. (1992) Angiotensin II stimulates the proliferation and biosynthesis of type I collagen in cultured murine mesangial cells. Am J Pathol 140:95–107.
Bell, L and JA Madri (1990) Influence of the angiotensin system on endothelial and smooth muscle cell migration. Am J Pathol 137:7–12.
Fernandez, LA et al. (1985) Neovascularization produced by angiotensin II. J Lab Clin Med 105:141.
LeNoble, FAC et al. (1991) Angiotensin II stimulates angiogenesis in the chorio–allantoic membrane of the chick embryo. Eur J Pharmacol 195:305–6.
Powell, JS et al. (1989) Inhibitors of angiotensin–converting enzyme prevent myointimal proliferation after vascular injury. Science 245:186–8.
Powell, JS et al. (1991) The proliferative response to vascular injury is suppressed by converting enzyme inhibition. J Cardiovasc Pharmacol 16 (suppl 4):42–9.
Capron, L et al. (1991) Effect of ramipril, an inhibitor of angiotensin converting enzyme, on the response of rat thoracic aorta to injury with a balloon catheter. J Cardiovasc Pharmacol 18:207–11.
Osterrieder, W. et al. (1991) Role of angiotensin II injury–induced neointima formation in rats. Hypertension 18:Suppl II60–64.
Daemen, MJAP et al. (1991) Angiotensin II induces smooth muscle cell proliferation in the normal and injured rat arterial wall. Circ Res 68:450–6.
Schelling, P et al. (1979) Effects of angiotensin II and angiotensin II antagonist saralysin on cell growth and renin in 3T3 and SV3T3 cells. J Cell Physiol 98:503–13.
Campbell–Boswell, M and AL Robertson. (1981) Effects of angiotensin II and vasopressin on human sooth muscle cells in vitro. Exp Mol Pathol 35:265–76.
Emmett, N et al. (1986) Effect of saralasin (angiotensin II antagonist) on 3T3 cell growth and proliferation. J Cell Biol 103:171 (Abst).
Paquet, JL et al. (1990) Angiotensin II–induced proliferation of aortic myocytes in spontaneously hypertensive rats. J Hypertens 8:565–72.
Geisterfer, AAT et al. (1988) Angiotensin II induces hypertrophy, not hyperplasia, of cultured rat aortic smooth muscle cells. Circ Res 62:749–56.
Naftilan, AJ (1992) The role of angiotensin II in vascular smooth muscle cell growth. J Cardiovas Pharmacol 20:S37–40.
Gibbons, GH et al. (1992) Vascular smooth muscle cell hypertrophy vs hyperplasia. Autocrine transforming growth factor–beta 1 expression determines growth response to angiotensin II. J Clin Invest 90:456–61.
Bell, L et al. (1992) Autocrine angiotensin system regulation of bovine aortic endothelial cell migration and plasminogen activator involves modulation of proto–oncogene pp60c–src expression. J Clin Invest 89:315–20.
Berk, BC and GN Rao. (1993) Angiotensin II–induced vascular smooth muscle cell hypertrophy: PDGF A–chain mediates the increase in size. J Cell Physiol 154:368–80.
Wolf, G et al. (1991) Intracellular signalling of transcription and secretion of type IV collagen after angiotensin II–induced cellular hypertrophy in cultured proximal tubular cells. Cell Reg 2:219–27.
Zhou, G et al. (1992) Antiotensin II mediated stimulation of collagen synthesis in cultured cardiac fibroblasts. FASEB J 6:A1914.
Kimura, B et al. (1992) Changes in skin angiotensin II receptors in rats during wound healing. BBRC 187:1083–1090.
Phillips et al. 1994. Angiotensin receptor stimulation of transforming growth factor–$\beta$ in rat skin and wound healing. In Angiotensin Receptors (ed JM Saavedra and PBMWM Timmermans), Plenum Press, New York, NY, pp. 377–396.
Wong, PC. 1994. Angiotensin antagonists in models of hypertension. In: Angiotensin Receptors (JM Saavedra and PBMWM Timmermans), Plenum Press NY, NY pp. 319–336.
MacKenzie et al. 1994. TCV 116 prevents progressive renal injury in rats with extensive renal ablation. J. Hypertension 12 (Suppl 9):S11–S16.
Gupta, et al. 1995. Locally generated angiotensin II in the adrenal gland regulates basal, corticotropin and potassium–stimulaed aldosterone secretion. Hypertension 25:443–448.
Lloren–Cortes, et al. 1994. Tissular expression and regulation of type 1 angiotensin II receptor subtypes by quantitative reverse transcriptase–polymerase chain reaction analysis. Hypertension 24:538–548.
Pratt, RE et al. 1992. The AT2 isoforms of the angiotensin receptor mediates myointimal hyperplasia following vascular injury. Hypertension 20:432.
Viswanathan, M et al. Balloon angioplasty enhances the expression of angiotensin II subtype AT1 receptors in the neointima of rat aorta. J Clin Invest 90:1707–12, 1992.
Viswanathan, M, and JM Saavedra (1992) Expressin of Angiotensin II $AT_2$ Receptors in the Rat Skin During Experimental Wound Healing. Peptides 13:783–6.
Janiak et al. 1992. Role of angiotensin subtype 2 receptor in neointima formation after vascular injury. Hypertension 20:737–45.
Forney Prescott et al. 1991. Angiotensin–converting enzyme inhibitor versus angiotensin II, AT1 receptor antagonist. Effect on smooth muscle cell migration and proliferation after ballon catheter injury. Am J Pathol 139:1291–6.
Kauffman, et al. 1991. Losartan, a nonpeptide angiotensin II (Ang II) receptor antagonist, inhibits neointima formation following balloon injury to rat carotid arteries. Life Sci 49:223–228.
Regoli, D. et al. (1974) Pharmacology of Angiotensin. Pharmacological Reviews 26:69.
Widdop et al. 1992. Electrophysiological Responses of Angiotensin Peptides on the Rat Isolated Nodose Ganglion. Clin and Exper. Hyper.–Theory and Practice, A14(4), 597–613.

Jaiswal et al. 1991. Subtype 2 angiotensin receptors mediate prostaglandin synthesis in human astrocytes. Hypertension 17:1115–1120.

Ferrario et al. 1991. Angiotensin–(1–7): A new hormone of the angiotensin system. Hypertension 19[suppl III]:III–126–III–133.

Ambuhl et al. 1992. Effects of angiotensin analogues and angiotensin receptor antagonists on paraventricular neurones. Regulatory Peptides 38:111–120.

Schiavone et al. 1990. Angiotensin–[1–7]: Evidence for novel actions in the brain. J Cardiovascular Pharmacol 16(Suppl 4):S19–S24.

Benter et al. 1993. Cardiovascular actions of angiotensin(1–7), Peptides 14:679–684.

Andreatta–Van Leyen, S et al. 1993. Modulation of phospholipase A2 activity and sodium transport by angiotensin–(1–7). Kidney International 44:932–6.

Moriguchi, A et al. 1994. Differential regulation of central vasporessin in transgenic rats harboring the mouse Ren–2 gene. Am J Physiol 267:R786–R791.

Porsti et al. 1994. Release of nitric oxide by angiotensin–(1–7) from porcine coronary endothelium: implications for a novel angiotensin receptor. Br. J Pharmacol. 111:652–654.

Cheng et al. 1994. Comparison of pressor responses to angiotensin I, II and III in pulmonary vascular bed of cats. Am. J Physiol 266:H2247–H2255.

Jaiswal et al. 1993. Differential regulation by angiotensin peptides in porcine aortic smooth muscle cells: subtypes of angiotension receptors involved. J. Pharmacol and Exp Therapeutic 265:664–673.

Edwards, RM and EJ Stack. 1993. Angiotensin II inhibits glomerular adenylate cyclase via the angiotensin II receptor subtype 1 (AT1). J Pharmacol Exper Ther 266:506–510.

Jaiswal et al. 1992. Stimulation of endothelial cell prostaglandin production by angiotensin peptides. Characterization of receptors. Hypertensin 19 (Suppl II):II–49–II–55.

Webb et al. 1992. Molecular characterization of angiotensin II type II receptors in rat pheochromocytoma cells. Peptides 13:499–508.

Pfeilschifter et al. 1992. Angiotensin II stimulation of phospholipase D in rat renal mesangial cells is mediated by the AT1 receptor subtype. Eur J Pharmacol 225:57–62.

Wong et al. 1992. Enhancement of Iosartan (DuP 753)–induced Angiotensin II Receptor Antagonism by PD123177 in Rats. European Journal of Pharmacology, 220:267–270.

Fitzsimons, JT. 1971. The effect on drinking of peptide precursors and of shorter chain peptide fragments of angiotensin II injected into the rat's diencephalon. J Physiol 214:295–303.

Wright et al. 1989. Structure–function analyses of brain angiotensin control of pressor action in rats. Am J Physiol 257:R1551–R1557.

Timmermans et al., "Angiotensin II Receptors Subtypes", *Am. J. Hypertens* 5 (6 part 1), 1992, 406–410, (abstract).

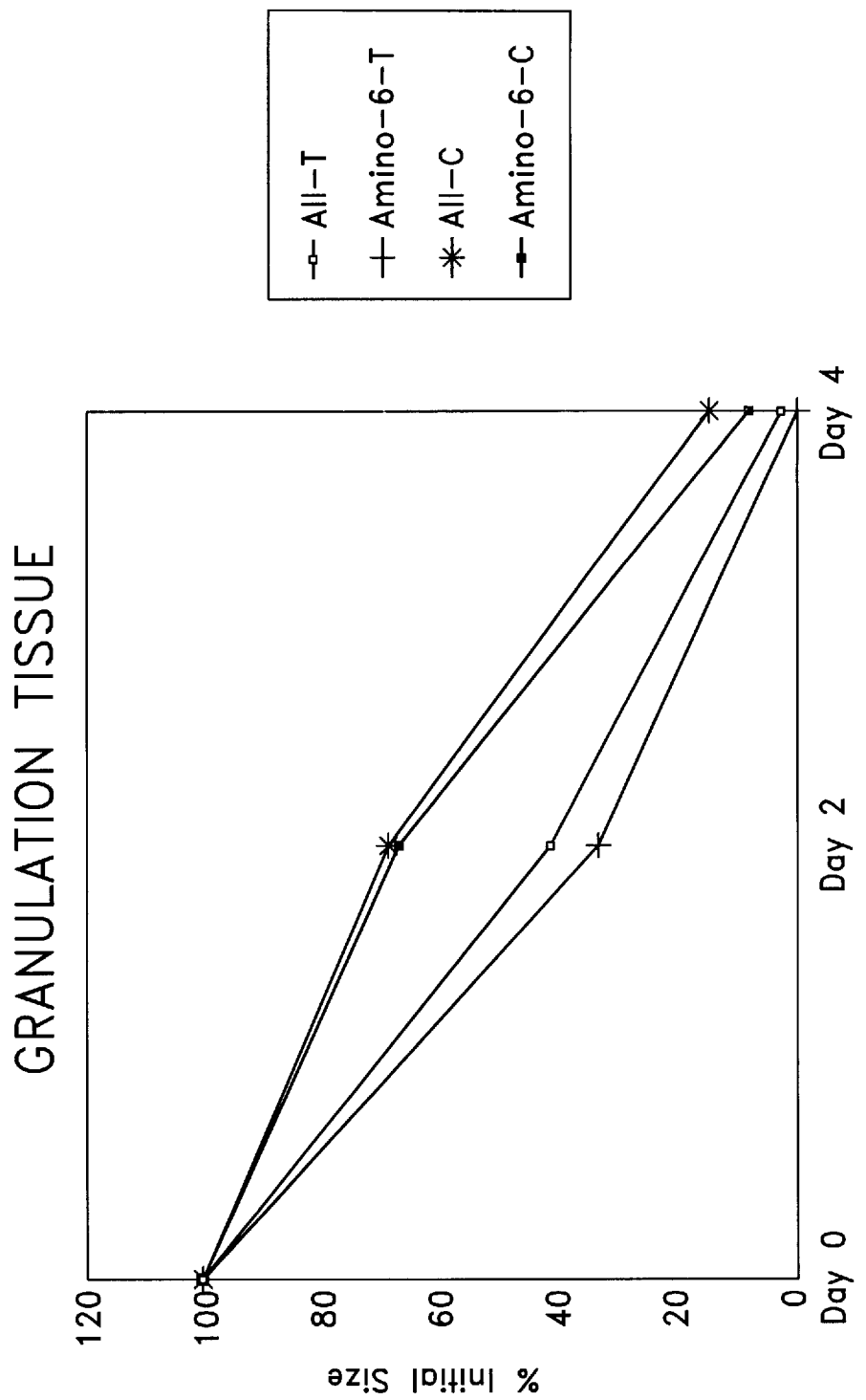

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asp Arg Val Tyr Ile His Pro Phe
1               5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Other
        ( B ) LOCATION: 6...6
        ( D ) OTHER INFORMATION: Position 6 is p-amino-Phe ( x i ) SEQUENCE DESCRIPTION: SEQ ID NO:2:

Asp Arg Val Tyr Ile Xaa Pro Phe
1               5

USE OF ANGIOTENSIN II TYPE 2 RECEPTOR AGONISTS IN TISSUE REPAIR

BACKGROUND OF THE INVENTION

This invention relates generally to the fields of biochemistry and medicine. More particularly, the present invention relates to methods and substances for use in accelerating the growth or healing of tissue.

Wounds (i.e., lacerations or openings) in mammalian tissue result in tissue disruption and coagulation of the microvasculature at the wound face. Repair of such tissue represents an orderly, controlled cellular response to injury. All soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in great detail and have in some instances been quantified [Hunt, T. K. et al., "Coagulation and macrophage stimulation of angiogenesis and wound healing," in *The surgical wound*, pp. 1–18, ed. F. Dineen & G. Hildrick-Smith (Lea & Febiger, Philadelphia: 1981)].

The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). While this new blood vessel growth (angiogenesis) is necessary for the healing of wound tissue, angiogenic agents are in general unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of angiotensin II to wound tissue significantly increases the rate of wound healing, leading to a more rapid re-epithelialization and tissue repair. The term angiotensin II refers to an octapeptide present in humans and other species having the sequence Asp-Arg-Val-Tyr-Ile-His-Pro-Phe [SEQ ID NO:1]. Angiotensin II is a known pressor agent and is commercially available.

Despite the utility of angiotensin II in accelerating wound healing, there remains a need for additional agents which are useful in promoting wound healing. Moreover, it would be highly advantageous to employ an agent which is less potent than angiotensin II at inducing hypertension.

PCT Patent Applications PCT/US94/10502 and PCT/US94/10503 disclose the use in wound repair of compositions comprising angiotensin II analogs and angiotensin III and analogs thereof, respectively. While these compositions have clear utility in wound treatment, there remains a need for compositions and methods with which fewer undesired side-effects may be associated.

A peptide agonist selective for the AT2 receptor (the peptide has 1000×higher affinity for AT2 than AT1) has been identified. This peptide is p-aminophenylalanine 6-AII ["(p-NH$_2$-Phe)6-AII"], Asp-Arg-Val-Tyr-Ile-Xaa-Pro-Phe [SEQ ID NO:2] wherein Xaa is p-NH$_2$-Phe [Speth, RC and KH Kim. 1990. Discrimination of two angiotensin II receptor subtypes with a selective agonist analogue of angiotensin II, p-aminophenylalanine6 angiotensin II. Biochem Biophys Res Commun 169:997–1006]. This peptide gave binding characteristics comparable to the AT2 antagonists in the experimental models tested [Catalioto et al. 1994. Angiotensins induce the release of prostacyclin from rabbit vas deferens: evidence for receptor heterogeneity. Eur J Pharmacol 256:93–97; Bryson, SE et al. 1992. Induction of the angiotensin At2 receptor subtype expression by differentiation of the neuroblastoma x glioma hybrid, NG-108-15. Eur J Pharmacol 225:119–127].

It is an object of the present invention to provide compositions and methods which do not suffer from all of the drawbacks of the heretofore-known compositions.

SUMMARY OF THE INVENTION

The present invention relates to the use of angiotensin II Type 2 receptor agonists ("AT2 agonist") in wound healing. These compounds form the basis of compositions useful for accelerating wound healing, the compositions comprising at least one AT2 agonist in an amount effective to accelerate wound healing. Agonists of the AT2 receptor subtype are of benefit in wound repair but do not exhibit many of the side effects of angiotensin II, such as increases in blood pressure and thirst. Preferably, the compositions are in the form of matrical or micellar solutions.

BRIEF DESCRIPTION OF THE DRAWINGS

The invention may be better understood with reference to the accompanying drawings, in which:

FIG. 2 illustrates the percent of increase in the formation of granulation tissue relative to a vehicle-treated control using (p-NH$_2$-Phe)6-AII.

DETAILED DESCRIPTION OF THE INVENTION

Figure 1:
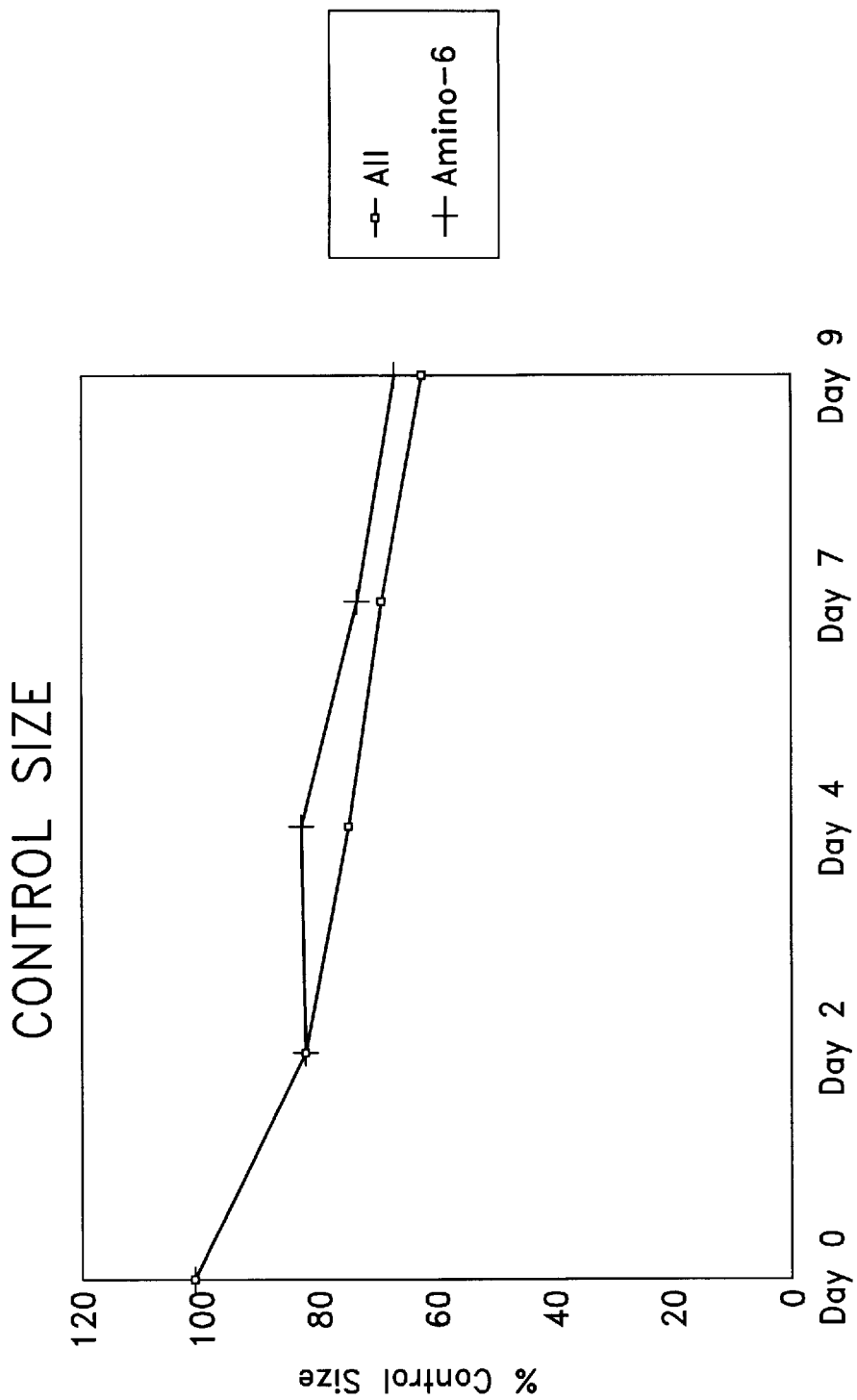
FIG. 1 illustrates the percent of control response in wound closure relative to a vehicle-treated control using (p-NH$_2$-Phe)6-AII.

Pursuant to the present invention, wound healing in mammalian tissue is promoted through the use of a composition comprising an effective amount of at least one AT2 agonist. The active agent is generally administered in a matrical or micellar solution and is effective in accelerating re-epithelialization and tissue repair even in very low concentrations.

As hereinafter defined, a preferred class of AT2 agonists for use in accordance with the present invention comprises AII analogs or active fragments thereof having p-NH$_2$-Phe in a position corresponding to position 6 of AII. In addition to peptide agents, various nonpeptidic agents (e.g., peptidomimetics) having the requisite AT2 agonist activity are further contemplated for use in accordance with the present invention.

Angiotensin II is one of the most potent vasoconstrictors known, causing constriction of the small arteries that branch to form the capillaries, i.e., the arterioles. The biological formation of angiotensin is initiated by the action of renin on the plasma substrate angiotensinogen. The substance so formed is a decapeptide called angiotensin I which is converted to angiotensin II by the converting enzyme angiotensinase that removes the C-terminal His-Leu residues from angiotensin I.

Recent studies have shown that the vasoactive product of the renin-angiotensin system, angiotensin II (AII), increases the release of growth factors, mitogenesis, chemotaxis and the release of extracellular matrices of cultured cells that are involved in wound repair [Dzau V. E. et al. (1989) Molecular mechanism of angiotensin in the regulation of vascular and cardiac growth. J Mol Cell Cardiol 21 (Supple III):S7; Berk, BC et al. (1989) Angiotensin II stimulated protein synthesis in cultured vascular smooth muscle cells. Hypertension 13:305–14; Kawahara, Y, et al. (1988) Angiotensin II induces expression of the c-fos gene through protein kinase C activation and calcium ion mobilization in cultured vascular smooth muscle cells. BBRC 150:52–9; Naftilan, AJ et al. (1989) Induction of platelet-derived growth factor A-chain and c-myc gene expressions by angiotensin II in cultured rat vascular smooth muscle cells. J Clin Invest 83:1419–24; Taubman, MB et al. (1989) Angiotensin II induces c-fos mRNA in aortic smooth muscle. Role of $Ca^{2+}$ mobilization and protein kinase C activation. J Biol Chem 264:526–530; Nakahara, K et al. (1992) Identification of three types of PDGF-A chain gene transcripts in rabbit vascular smooth muscle and their regulated expression during development and by angiotensin II. BBRC 184:811–8; Stouffer GA and GK Owens. (1992) Angiotensin II induced mitogenesis of spontaneously hypertensive rat derived cultured smooth muscle cells is dependent on autocrine production of transforming growth factor-β. Circ Res 70:820; Wolf, G et al. (1992) Angiotensin II stimulates the proliferation and biosynthesis of type I collagen in cultured murine mesangial cells. Am J Pathol 140:95–107; Bell, L and JA Madri (1990) Influence of the angiotensin system on endothelial and smooth muscle cell migration. Am J Pathol 137:7–12]. In addition, AII was shown to be angiogenic in rabbit corneal eye and chick chorioall antoic membrane models (Fernandez, LA et al. (1985) Neovascul arization produced by angiotensin II. J Lab Clin Med 105–141; LeNoble, FAC et al. (1991) Angiotensin II stimulates angiogenesis in the chorio-allantoic membrane of the chick embryo. Eur J Pharmacol 195:305–6 ]. Therefore, AII may accelerate wound repair through increased neovascularization, growth factor release, reepithelialization and production of extracellular matrix. Through an increase in the flow of blood and nutrients to an injured tissue, AII may increase the rate of wound repair. AII may also accelerate wound repair through the generation of growth factors at the site of injury. Exogenous addition of growth factors has been shown to accelerate wound repair through a variety of mechanisms [Grotendorst, GR et al. (1985) Stimulation of granulation tissue formation by platelet-derived growth factor in normal and diabetic rats. J Clin Invest 76:2323–9; Mustoe, TA et al. (1987) Accelerated healing of incisional wounds in rats induced by transforming growth factor-β. Science 237:1333–5; Pierce, GF et al. (1988) In vivo incisional wound healing augmented by platelet-derived growth factor and recombinant c-sis gene homodimeric proteins. J Exp Med 167:974–87; Lynch, SE et al. (1989) Growth factors in wound healing. J Clin Invest 84:640–6; Greenhalgh, DG et al. (1990) PDGF and FGF stimulate wound healing in the genetically diabetic mouse. Am J Pathol 136:1235–46]. Recent studies showed that AII increased neointima formation in the carotid artery and aorta after injury [Powell, JS et al. (1989) Inhibitors of angiotensin-converting enzyme prevent myointimal proliferation after vascular injury. Science 245:186–8; Powell, JS et al. (1991) The proliferative response to vascular injury is suppressed by converting enzyme inhibition. J Cardiovasc Pharmacol 16 (suppl 4):S42–9; Capron, L et al. (1991) Effect of ramipril, an inhibitor of angiotensin converting enzyme, on the response of rat thoracic aorta to injury with a balloon catheter. J Cardiov wsc Pharmacol 18:207–11; Osterriedes, W et al. (1991) Role of angiotensin II injury-induced neointima formation in rats. Hypertension 18:Suppl II60–64; Daemen, MJAP et al. (1991) Angiotensin II induces smooth muscle cell proliferation in the normal and injured rat arterial wall. Circ Res 68:450–6]. As a result of these observations, studies were conducted to determine the mechanism by which endogenous AII may induce intimal hyperplasia. AII was shown to act as a mitogen for smooth muscle cells, fibroblasts and endothelial cells [Schelling, P et al. (1979) Effects of angiotensin II and angiotensin II antagonist saralysin on cell growth and renin in 3T3 and SV3T3 cells. J Cell Physiol 98:503–13; Campbell-Boswell, M and AL Robertson. (1981) Effects of angiotensin II and vasopressin on human smooth muscle cells in vitro. Exp Mol Pathol 35:265–76; Emmett, N et al. (1986) Effect of saralasin (angiotensin II antagonist) on 3T3 cell growth and proliferation. J Cell Biol 103:171 (Abst); Paquet, JL et al. (1990) Angiotensin II-induced proliferation of aortic myocytes in spontaneously hypertensive rats. J Hypertens 8:565–72; Dzau et al, supra]. AII also increased the protein content and size of vascular smooth muscle cells [Berk et al. (1989), supra; Geisterfer, AAT et al. (1988) Angiotensin II induces hypertrophy, not hyperplasia, of cultured rat aortic smooth muscle cells. Circ Res 62:749–56]. Studies showed that AII increases the release of growth factors of various types, including PDGF, heparin-binding EGF and transforming growth factor-β (TGFβ), and growth-related proto-oncogenes from smooth muscle cells, endothelial cells and cardiac fibroblasts [Kawahara et al. (1988), supra; Naftilan, AJ (1992) The role of angiotensin II in vascular smooth muscle cell growth. J Cardiovas Pharmacol 20:S37–40; Naftilan et al. (1989), supra; Taubman et al. (1989), supra; Nakahara et al. (1992), supra; Temizer et al (1992), supra; Gibbons, GH et al. (1992) Vascular smooth muscle cell hypertrophy vs hyperplasia. Autocrine transforming growth factor-beta 1 expression determines growth response to angiotensin II. J Clin Invest 90:456–61; Bell, L et al. (1992) Autocrine angiotensin system regulation of bovine aortic endothelial cell migration and plasminogen activator involves modulation of proto-oncogene pp60-src expression. J Clin Invest 89:315–20; Stouffer and Owens (1992), supra]. The hypertrophy of vascular smooth muscle cells by AII was mediated through PDGF [Berk, BC and GN Rao. (1993) Angiotensin II-induced vascular smooth muscle cell hypertrophy: PDGF A-chain mediates the increase in size. J Cell Physiol 154:368–80].

Therefore, it is conceivable that AII acts to accelerate wound repair through increasing the levels of these growth factors in the wound tissue. Additionally, AII was shown to stimulate collagen synthesis thereby suggesting a role for this factor in extracellular matrix formation [Wolf, G et al. (1991) Intracellular signaling of transcription and secretion of type IV collagen after angiotensin II-induced cellular hypertrophy in cultured proximal tubular cells. Cell Reg 2:219–27; Wolf et al. (1992), supra; Zhou, G et al. (1992) Angiotensin II mediated stimulation of collagen synthesis in cultured cardiac fibroblasts. FASEB J 6:A 1914]. Wound repair also involves chemotaxis of the necessary cell types into the wound bed. AII was also shown to induce the migration of endothelial cells and smooth muscle cells in vitro [Bell and Madri (1990), supra ].

Recent studies also indicate that expression of AII receptors is altered during the process of wound repair [Viswanathan, M, and JM Saavedra (1992) Expression of Angiotensin II AT$_2$ Receptors in the Rat Skin During Experimental Wound Healing. Peptides 13:783–6; Kimura, B et al. (1992) Chinges in skin angiotensin II receptors in rats during wound healing. BBRC 187:1083–1090]. These changes, along with evidence of an increase in the local production of AII at the site of repair, suggests that AII may play a key role in the process of wound repair.

The actions of AII that may be involved in wound repair have recently been reviewed [Phillips et al. 1994. Angiotensin receptor stimulation of transforming growth factor-β in rat skin and wound healing. In Angiotensin Receptors (ed JM Saavedra and PBMWM Timmermans), Plenum Press, New York, N.Y, pp 377–396]. In the majority of studies reported, these effects have been shown to be mediated by the AT1 receptor.

The blood pressure effects (and most other effects, such as aldosterone secretion and increased thirst) of angiotensin II (AII) are mediated by the type 1 receptor (AT1 receptor) [Wong, PC. 1994. Angiotensin antagonists in models of hypertension. In: Angiotensin Receptors (JM Saavedra and PBMWM Timmermans), Plenum Press N.Y., N.Y. pp 319–336; MacKenzie et al. 1994. TCV 116 prevents progressive renal injury in rats with extensive renal ablation. J. Hypertension 12 (Suppl 9):S11–S16; Gupta, et al. 1995. Locally generated angiotensin II in the adrenal gland regulates basal, corticotropin and potassium-stimulated aldosterone secretion. Hypertension 25:443–448; Llorens-Cortes, et al. 1994. Tissular expression and regulation of type 1 angiotensin II receptor subtypes by quantitative reverse transcriptase-polymerase chain reaction analysis. Hypertension 24:538–548; Wong, et al. 1992. Enhancement of losartan (Dup 753)-induced angiotensin II receptor antagonism by PD 123177 in rats. Eur J Pharmacol 220:267–70]. This conclusion is based upon the blocking of the action of AII by receptor subtype specific antagonists.

The effects of AII and AII antagonists have been examined in two experimental models of vascular injury and repair. Studies have been mixed with regards to the contribution of AT2 to hyperplasia of vessels after balloon injury to the vasculature. In the rat carotid artery, the majority of receptors are to the AT1 subtype. Two weeks after balloon injury, the majority of receptors are AT2 [Pratt, RE et al. 1992. The AT2 isoforms of the angiotensin receptor mediates myointimal hyperplasia following vascular injury. Hypertension 20:432]. By contrast, neointimal cells of the injured rat thoracic aorta express predominantly AT1 receptors [Viswanathan, M et al. Balloon angioplasty enhances the expression of angiotensin II subtype AT1 receptors in the neointima of rat aorta. J Clin Invest 90:1707–12, 1992]. Treatment of rats with PD 123319 (AT2 specific antagonist) reduced intimal hyperplasia by 73% while losartan (ATI specific antagonist) decreased intimal area by 95% [Pratt et al. (1992), supra]. In a similar model, CGP 42112 (AT2 antagonist) infused perivascularly for 14 days prevented neointimal formation, but low doses of losartan were ineffective [Janiak et al. 1992. Role of angiotensin subtype 2 receptor in neointima formation after vascular injury. Hypertension 20:737–45]. In other studies, losartan at higher doses was found to be effective [Forney Prescott et al. 1991. Angiotensin-converting enzyme inhibitor versus angiotensin II, AT1 receptor antagonist. Effect on smooth muscle cell migration and proliferation after balloon catheter injury. Am J Pathol 139:1291–6; Kauffman, et al. 1991. Losartan, a nonpeptide angiotensin II (Ang II ) receptor antagonist, inhibits neointima formation following balloon injury to rat carotid arteries. Life Sci 49:223–228]. Therefore, it is conceivable that both receptor subtypes may play a role in the formation of vascular lesions after balloon injury.

During experimental wound healing, the expression of AII receptors increase significantly in a localized band of tissue within the superficial dermis of the skin surrounding the wound; the major proportion of the increase is due to AT2 receptor [Viswanathan, et al. 1992. Expression of angiotensin II AT2 receptors in the rat skin during experimental wound healing. Peptides 13:783–6; Kimura et al. Changes in skin angiotensin II receptors in rats during wound healing. Biochem Biophys Res Commun 187:1083–90]. These studies were done in young rats that express some AT2 receptors. In wound healing studies in adult rats (as are used in the experiments reported herein), AT1 receptors are altered after an incisional wound. The experimental designs in these latter studies do not distinguish between the dermis and other portions of the wound.

A preferred class of AT2 agonists have the general formula

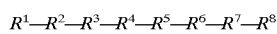

in which $R^1$ and $R^2$ together form a group of formula

wherein X is H or a one to three peptide group and a peptide bond between $R^A$ and $R^B$ is labile to aminopeptidase A cleavage;

$R^3$ is selected from the group consisting of Val, Ala, Leu, Ile, Gly, Pro, Aib, Acpc and Tyr;

$R^4$ is selected from the group consisting of Tyr, Thr, Ser and azaTyr;

$R^5$ is selected from the group consisting of Ile, Ala, Leu, Val and Gly;

$R^6$ is p-NH$_2$-Phe;

$R^7$ is Pro or Ala; and $R^8$ is selected from the group consisting of Phe, Phe(Br), Ile and Tyr.

In one class of preferred embodiments, $R^A$ is suitably selected from Asp, Glu, Asn, Acpc (1-aminocyclopentane carboxylic acid), Ala, Me$^2$Gly, Pro, Bet, Glu(NH$_2$), Gly, Asp(NH$_2$) and Suc. $R^B$ is suitably selected from Arg, Lys, Ala, Orn, Ser(Ac), Sar, D-Arg and D-Lys. Particularly preferred combinations for $R^A$ and $R^B$ are Asp-Arg, Asp-Lys, Glu-Arg and GIL-Lys.

In the above formulas, the standard three-letter abbreviations for amino acid residues are employed. In the absence of an indication to the contrary, the L-form of the amino acid is intended. Other residues are abbreviated as follows:

| | |
|---|---|
| Me$^2$Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogs adopt either a gamma or a beta turn [Regoli, D. et al. (1974) Pharmacology of Angiotensin. Pharmacological Reviews 26:69]. In general, it is believed that neutral side chains in positions $R^3$, $R^5$ and $R^7$ may be involved in maintaining the appropriate distance between the active groups in positions $R^4$, $R^6$ and $R^8$ primarily responsible for binding to receptors and/or intrinsic activity. Hydrophobic side chains in positions $R^3$, $R^5$ and $R^8$ may also play an important role on the whole conformation of the peptide and/or contribute to formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or non-linear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, Ile, Gly, Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Ser and azaTyr. In this position, Tyr is particularly preferred as it may form a hydrogen bond with the receptor site capable of accepting a hydrogen from the phenolic hydroxyl [Regoli et al. (1974), supra].

In position $R^5$, an amino acid with a β aliphatic or alicyclic chain is particularly desirable. Therefore, while Gly is suitable in position $R^5$, it is preferred that the amino acid in this position be selected from Ie, Ala, Leu and Val.

In the compounds of particular interest in accordance with the present invention, $R^6$ is p-$NH_2$-Phe; the literature suggests that this amino acid confers agonist activity. It is presently considered that $R^7$ should be Pro in order to provide the most desirable orientation of $R^8$. In position $R^8$, both a hydrophobic ring and an anionic carboxyl terminal appear to be particularly useful in binding of the analogs of interest to receptors; therefore, Tyr and especially Phe are preferred for purposes of the present invention.

The AT2 agonist p-aminophenylalanine6-AII was tested in a rat model for dermal repair and gave results comparable to AII at a dose of 100 μg/d for 5 days. Both granulation tissue formation and wound closure were examined and found to be accelerated by p-aminophenylalanine6-AII.

According to the method of the invention, at least one AT2 agonist is applied to wound tissue in amounts sufficient to increase the healing rate of tissue. These compounds can significantly accelerate the rate of healing at nanomolar levels in vivo. For any given agonist (peptidic or nonpeptidic), optimum levels for use in a given formulation may readily be determined empirically. In general, an amount of active agent suitable for use in accordance with the present invention ranges from about 0.0001 μg to about 10 mg per kilogram body weight.

The compounds of the invention may be applied in a variety of solutions. Suitable solutions for use in accordance with the present invention are sterile, dissolve sufficient amounts of the peptide, and are not harmful to wound tissue. In this regard, the compounds of the present invention are very stable but are hydrolyzed by strong acids and bases. The compounds of the present invention are soluble in organic solvents and in aqueous solutions at pH 5–8.

Any type of application means may be employed which permits the influx of the active agents into the tissue over a period of time. For example, an aqueous solution could be applied to the wound tissue through a gauze bandage or strip, or such a Solution could be formulated so that a timed perfusion may be obtained (using, e.g., liposomes, ointments, micelles, etc). Methods for the production of these formulations with the compounds of the present invention are apparent to those of ordinary skill in the art. The particular concentration of active agent employed is not critical, as the tissue-repairing effect is present even when the compounds are present in nanogram quantities.

Preferably, a matrical or micellar solution is employed with the active agent present in a concentration of at least 1 milligram per milliliter. A particular matrical solution which has been used to advantage is a semi-solid polyethylene glycol polymer sold under the trademark Hydron by Hydro Med Sciences, New Brunswick, N.J. Another preferred solution is a micellar solution sold under the trade name Pluronics F108 by BASF, Ludwigshafen, Germany. Under room temperature conditions, this solution is a liquid, but when applied to warm tissue the solution forms a gel which permits the infusion of active agent into the wound tissue for a period of several days. Other preferred formulations include carboxymethyl cellulose preparations (as used in the example herein), crystalloid preparations (e.g., saline, Ringer's lactate solution, phosphate-buffered saline, etc.), viscoelastics, polyethylene glycols, polypropylene glycols and wound dressings (e.g., bandages, etc.).

The healing effects of the compounds of the present invention may be provided in a variety of instances. The solution may be applied topically to surface wound tissue in the treatment of ulcers, lesions, injuries, diabetic ulcers, burns, trauma, stasis ulcers, periodontal conditions, lacerations and other conditions. In addition, intraperitoneal wound tissue such as that resulting from invasive surgery may be treated with a composition in accordance with the present invention to accelerate healing. For example, following the surgical removal of a colon section or other tissue, the surgical plane may be coated with a solution of active agent prior to closing the surgical site in order to accelerate internal capillary perfusion and healing. In addition, the rate of localized healing may be increased by the subdermal administration of active agent by injection or otherwise.

The invention may be better understood with reference to the accompanying example, which is intended for purposes of illustration only and should not be construed as in any sense limiting the scope of the invention as defined in the claims appended hereto.

Example

Female Sprague Dawley rats, 175–200 g, were obtained from Simonsen Laboratories, Gilroy, Calif. On the day of surgery, the rats received intramuscular ketamine/rompum anesthesia prior to preparation for surgery. The rats were shaved and scrubbed with betadine. Two 1.5×1.5 cm full thickness dermal wounds were created on the dorsal surface of the rat. Following excision of the skin, the size of the wound was outlined on a glass slide and the medicament was administered in 100 μl 10% low viscosity carboxymethyl cellulose (Sigma). The test materials were administered in a randomized fashion; all materials were tested at 100 μg/wound. Controls were treated with vehicle only. After administration of the materials, the rats were bandaged and allowed to recover from anesthesia. On days 1–4 after surgery, the rats were treated with an additional 100 μg of peptide formulation. At days 2, 4, 7 and 9, the area of the skin wounds were measured under methoxyflurane anesthesia (commercially available as Metofane from Pittman-Moore, Mundelein, Ill.). The area of the wound was determined by: (1) tracing the wound shape onto graph paper (1×1 mm squares); (2) cutting out the shape; (3) weighing the paper and comparing the weight with a 1.5×1.5 cm paper cutout; and (4) counting the number of squares. In addition, on days 2, 4 and 7, the area of granulation tissue was similarly determined.

As illustrated in FIGS. 1–2, wound closure and the formation of granulation tissue was substantially accelerated relative to the control animals when the test animals were treated with an AT2 agonist. FIG. 1 illustrates the percent of control response in wound closure relative to a vehicle-treated control; FIG. 2 illustrates the percent increase in formation of granulation tissue relative to a vehicle control.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

cleavage; $R^3$ is selected from the group consisting of Val, Ala, Leu, Ile, Gly, Pro, Aib, Acpc and Tyr;

$R^4$ is selected from the group consisting of Tyr, Thr, Ser and azaTyr;

$R^5$ is selected from the group consisting of Ile, Ala, Leu, Val and Gly;

$R^6$ is p-$NH_2$-Phe;

$R^7$ is Pro or Ala; and $R^8$ is selected from the group consisting of Phe, Phe(Br), Ile and Tyr.

2. A method according to claim 1, wherein the compound of general formula I is (p-$NH_2$-Phe)6-AII.

3. A method according to claim 1, wherein the agonist is administered in a matrical or micellar solution.

What is claimed is:

1. A method of accelerating wound healing, comprising applying to a wound an amount effective to accelerate wound healing of at least one angiotensin II Type 2 receptor agonist other than angiotensin II, wherein the agonist has the formula $$R^1-R^2-R^3-R^4-R^5-R^6-R^7-R^8$$

in which $R^1$ and $R^2$ together form a group of formula $$X-R^A-R^B-,$$

wherein X is H or a one to three peptide group and a peptide bond between $R^A$ and $R^B$ is labile to aminopeptidase A 4. A method according to claim 1, wherein the agonist is administered at a rate of at least 0.1 ng per kg body weight in a suitable carrier or diluent.

5. A method according to claim 4, wherein the carrier or diluent is selected from the group consisting of carboxymethyl cellulose preparations, crystalloid preparations, viscoelastics, polyethylene glycols and polypropylene glycols.

6. A method according to claim 1, wherein the agonist is administered in conjunction with a wound dressing.

* * * * *